(12) United States Patent
Hegeman et al.

(10) Patent No.: US 7,862,554 B2
(45) Date of Patent: Jan. 4, 2011

(54) ARTICULATING TOOL WITH IMPROVED TENSION MEMBER SYSTEM

(75) Inventors: David Elias Hegeman, San Jose, CA (US); David J. Danitz, San Jose, CA (US); Karrie S. Bertsch, San Jose, CA (US); Lincoln J. Alvord, Redwood City, CA (US); Cameron D. Hinman, Thurmond, NC (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 863 days.

(21) Appl. No.: 11/787,608

(22) Filed: Apr. 16, 2007

(65) Prior Publication Data

US 2008/0255421 A1 Oct. 16, 2008

(51) Int. Cl.
*A61B 1/008* (2006.01)
(52) U.S. Cl. .......................................... 606/1; 600/139
(58) Field of Classification Search ............ 606/1; 600/139, 141
See application file for complete search history.

(56) References Cited

U.S. PATENT DOCUMENTS

| | | |
|---|---|---|
| 1,820,463 A | 8/1931 | Klein |
| 3,060,972 A | 10/1962 | Sheldon |
| 3,071,161 A | 1/1963 | Ulrich |
| 3,190,286 A | 6/1965 | Stokes |
| 3,557,780 A | 1/1971 | Sato |
| 3,605,725 A | 9/1971 | Bentov |
| 4,466,649 A | 8/1984 | Ozawa |
| 4,489,826 A | 12/1984 | Dubson |
| 4,580,551 A | 4/1986 | Siegmund et al. |
| 4,700,693 A | 10/1987 | Lia et al. |
| 4,763,669 A | 8/1988 | Jaeger |

(Continued)

FOREIGN PATENT DOCUMENTS

EP 0 165 718 12/1985

(Continued)

OTHER PUBLICATIONS

Hinman et al.; U.S. Appl. No. 12/725,377 entitled "Articulating mechanism with flex-hinged links," filed Mar. 16, 2010.

(Continued)

*Primary Examiner*—Henry M Johnson, III
*Assistant Examiner*—Jeffrey B Lipitz

(57) ABSTRACT

The invention provides surgical or diagnostic tools and associated methods that offer improved user control for operating remotely within regions of the body, and improved methods of assembling the tools. In some embodiments these tools include a proximally-located actuator for the operation of a distal end effector, as well as proximally-located actuators for articulational and rotational movements of the end effector. Control mechanisms and methods refine operator control of end effector actuation and of these articulational and rotational movements. The articulation mechanisms comprise pairs of links, one link distal and the other proximal, configured such that movement of a proximal link is transferred to the distal link by way of tension bearing members. Embodiments of the invention include a guide for such tension bearing members that facilitates assembly of the tool. Embodiments also include improved methods for attaching tension bearing members to the links. The inventions disclosed herein may also be used with articulating devices outside of the surgical and diagnostic fields.

27 Claims, 13 Drawing Sheets

U.S. PATENT DOCUMENTS

| | | |
|---|---|---|
| 4,790,294 A | 12/1988 | Allred et al. |
| 4,834,761 A | 5/1989 | Walters |
| 4,854,626 A | 8/1989 | Duke |
| 4,880,015 A | 11/1989 | Nierman |
| 4,984,951 A | 1/1991 | Jameson |
| 5,174,276 A | 12/1992 | Crockard |
| 5,257,618 A | 11/1993 | Kondo |
| 5,271,381 A | 12/1993 | Ailinger et al. |
| 5,273,026 A | 12/1993 | Wilk |
| 5,286,228 A | 2/1994 | Lee et al. |
| 5,297,443 A | 3/1994 | Wentz |
| 5,314,424 A | 5/1994 | Nicholas |
| 5,322,064 A | 6/1994 | Lundquist |
| 5,325,845 A | 7/1994 | Adair |
| 5,330,502 A | 7/1994 | Hassler et al. |
| 5,354,162 A | 10/1994 | Burdea et al. |
| 5,381,782 A | 1/1995 | DeLaRama et al. |
| 5,403,342 A | 4/1995 | Tovey et al. |
| 5,405,344 A | 4/1995 | Williamson et al. |
| 5,425,743 A | 6/1995 | Nicholas |
| 5,441,494 A | 8/1995 | Ortiz |
| 5,454,827 A | 10/1995 | Aust et al. |
| 5,476,479 A | 12/1995 | Green et al. |
| 5,486,154 A | 1/1996 | Kelleher |
| 5,490,819 A | 2/1996 | Nicholas et al. |
| 5,498,256 A | 3/1996 | Furnish |
| 5,513,827 A | 5/1996 | Michelson |
| 5,520,678 A | 5/1996 | Heckele et al. |
| 5,522,788 A | 6/1996 | Kuzmak |
| 5,549,636 A | 8/1996 | Li |
| 5,562,699 A | 10/1996 | Heimberger et al. |
| 5,570,919 A | 11/1996 | Eusebe |
| 5,599,151 A | 2/1997 | Daum et al. |
| 5,609,601 A | 3/1997 | Kolesa et al. |
| 5,620,415 A | 4/1997 | Lucey et al. |
| 5,624,398 A | 4/1997 | Smith et al. |
| 5,626,608 A | 5/1997 | Cuny et al. |
| 5,632,432 A | 5/1997 | Schulze et al. |
| 5,643,294 A | 7/1997 | Tovey et al. |
| 5,647,743 A | 7/1997 | Schmitt |
| 5,702,408 A | 12/1997 | Wales et al. |
| 5,704,534 A | 1/1998 | Huitema et al. |
| 5,713,505 A | 2/1998 | Huitema |
| 5,716,352 A | 2/1998 | Viola et al. |
| 5,759,151 A | 6/1998 | Sturges |
| 5,792,164 A | 8/1998 | Lakatos et al. |
| 5,807,376 A | 9/1998 | Viola et al. |
| 5,813,813 A | 9/1998 | Daum et al. |
| 5,823,066 A | 10/1998 | Huitema et al. |
| 5,827,323 A | 10/1998 | Klieman et al. |
| 5,836,960 A | 11/1998 | Kolesa et al. |
| 5,845,540 A | 12/1998 | Rosheim |
| 5,846,183 A | 12/1998 | Chilcoat |
| 5,873,817 A | 2/1999 | Kokish et al. |
| 5,899,425 A | 5/1999 | Corey et al. |
| 5,916,146 A | 6/1999 | Allotta et al. |
| 5,916,147 A | 6/1999 | Boury et al. |
| 5,921,956 A | 7/1999 | Grinberg et al. |
| 5,938,678 A | 8/1999 | Zirps et al. |
| 5,947,984 A | 9/1999 | Whipple |
| 5,961,532 A | 10/1999 | Finley et al. |
| 6,019,722 A | 2/2000 | Spence et al. |
| 6,050,996 A | 4/2000 | Schmaltz et al. |
| 6,161,543 A | 12/2000 | Cox et al. |
| 6,250,532 B1 | 6/2001 | Green et al. |
| 6,270,453 B1 | 8/2001 | Sakai |
| 6,446,850 B2 | 9/2002 | Ming-Shun |
| 6,464,704 B2 | 10/2002 | Schmaltz et al. |
| 6,471,641 B2 | 10/2002 | Sakamoto |
| 6,471,696 B1 | 10/2002 | Berube et al. |
| 6,482,149 B1 | 11/2002 | Torii |
| 6,491,626 B1 | 12/2002 | Stone et al. |
| 6,571,042 B1 | 5/2003 | Kordahi |
| 6,626,824 B2 | 9/2003 | Ruegg et al. |
| 6,635,071 B2 | 10/2003 | Boche et al. |
| 6,638,213 B2 | 10/2003 | Ogura et al. |
| 6,638,287 B2 | 10/2003 | Danitz et al. |
| RE38,335 E | 11/2003 | Aust et al. |
| 6,641,528 B2 | 11/2003 | Torii |
| 6,644,532 B2 | 11/2003 | Green et al. |
| 6,666,854 B1 | 12/2003 | Lange |
| 6,669,254 B2 | 12/2003 | Thom et al. |
| 6,676,676 B2 | 1/2004 | Danitz et al. |
| 6,682,541 B1 | 1/2004 | Gifford et al. |
| 6,743,239 B1 | 6/2004 | Kuehn et al. |
| 6,746,443 B1 | 6/2004 | Morley et al. |
| 6,749,560 B1 | 6/2004 | Konstorum et al. |
| 6,752,823 B2 | 6/2004 | Prestel |
| 6,764,445 B2 | 7/2004 | Ramans et al. |
| 6,773,327 B1 | 8/2004 | Felice et al. |
| 6,817,972 B2 | 11/2004 | Snow |
| 6,824,548 B2 | 11/2004 | Smith et al. |
| 6,843,794 B2 | 1/2005 | Sixto, Jr. et al. |
| 6,858,005 B2 * | 2/2005 | Ohline et al. ............... 600/141 |
| 6,902,560 B1 | 6/2005 | Morley et al. |
| 6,942,613 B2 | 9/2005 | Ewers et al. |
| 6,945,979 B2 | 9/2005 | Kortenbach et al. |
| 6,960,162 B2 | 11/2005 | Saadat et al. |
| 6,960,163 B2 | 11/2005 | Ewers et al. |
| 6,976,969 B2 | 12/2005 | Messerly |
| 6,994,700 B2 | 2/2006 | Elkins et al. |
| 7,138,976 B1 | 11/2006 | Bouzit et al. |
| 7,480,600 B2 | 1/2009 | Massie et al. |
| 7,553,275 B2 | 6/2009 | Padget et al. |
| 2001/0023313 A1 | 9/2001 | Ide |
| 2002/0096177 A1 | 7/2002 | Toti et al. |
| 2002/0111604 A1 | 8/2002 | Doyle et al. |
| 2002/0156497 A1 | 10/2002 | Nagase et al. |
| 2002/0161281 A1 | 10/2002 | Jaffe et al. |
| 2002/0177750 A1 | 11/2002 | Pilvisto |
| 2003/0036748 A1 | 2/2003 | Cooper et al. |
| 2003/0050649 A1 | 3/2003 | Brock et al. |
| 2003/0078644 A1 | 4/2003 | Phan |
| 2003/0109898 A1 | 6/2003 | Schwarz et al. |
| 2003/0114838 A1 | 6/2003 | O'Neill et al. |
| 2003/0135204 A1 | 7/2003 | Lee et al. |
| 2003/0149338 A1 | 8/2003 | Francois et al. |
| 2003/0153902 A1 | 8/2003 | Doyle et al. |
| 2003/0229271 A1 | 12/2003 | Briscoe et al. |
| 2003/0233026 A1 | 12/2003 | Saadat et al. |
| 2004/0054322 A1 | 3/2004 | Vargas |
| 2004/0138529 A1 | 7/2004 | Wiltshire et al. |
| 2004/0138700 A1 | 7/2004 | Cooper et al. |
| 2004/0236316 A1 | 11/2004 | Danitz et al. |
| 2005/0090809 A1 | 4/2005 | Cooper et al. |
| 2005/0096694 A1 | 5/2005 | Lee |
| 2005/0107667 A1 | 5/2005 | Danitz et al. |
| 2005/0119527 A1 | 6/2005 | Banik et al. |
| 2005/0251112 A1 | 11/2005 | Danitz et al. |
| 2005/0273084 A1 | 12/2005 | Hinman et al. |
| 2005/0273085 A1 | 12/2005 | Hinman et al. |
| 2006/0009759 A1 | 1/2006 | Chrisitian et al. |
| 2006/0020287 A1 | 1/2006 | Lee et al. |
| 2006/0036255 A1 | 2/2006 | Pond et al. |
| 2006/0058582 A1 | 3/2006 | Maahs et al. |
| 2006/0094931 A1 | 5/2006 | Danitz et al. |
| 2006/0111209 A1 | 5/2006 | Hinman et al. |
| 2006/0111210 A1 | 5/2006 | Hinman |
| 2006/0111615 A1 | 5/2006 | Danitz et al. |
| 2006/0111616 A1 | 5/2006 | Danitz |
| 2006/0199999 A1 * | 9/2006 | Ikeda et al. ............... 600/141 |
| 2006/0201130 A1 | 9/2006 | Danitz |
| 2007/0276430 A1 | 11/2007 | Lee et al. |
| 2008/0065116 A1 | 3/2008 | Lee et al. |

| | | | |
|---|---|---|---|
| 2008/0188869 A1* | 8/2008 | Weitzner et al. | 606/130 |
| 2008/0188871 A1* | 8/2008 | Smith et al. | 606/139 |

FOREIGN PATENT DOCUMENTS

| | | |
|---|---|---|
| EP | 0 598 618 A2 | 5/1994 |
| EP | 0 836 833 A2 | 4/1998 |
| EP | 1 132 041 A2 | 9/2001 |
| EP | 1 395 398 B1 | 3/2004 |
| JP | H06-262549 | 9/1994 |
| JP | 01-299768 | 10/2001 |
| WO | WO 01/10292 A1 | 2/2001 |
| WO | WO 02/13682 A1 | 2/2002 |
| WO | WO 2004/019769 A1 | 3/2004 |
| WO | WO 2004/105578 A3 | 12/2004 |
| WO | WO 2005/067785 A1 | 7/2005 |
| WO | WO 2005/120326 A3 | 12/2005 |
| WO | WO 2005/120327 A3 | 12/2005 |
| WO | WO 2006/057699 A1 | 6/2006 |
| WO | WO 2006/057700 A1 | 6/2006 |
| WO | WO 2006/057702 A2 | 6/2006 |
| WO | WO 2006/073581 A1 | 7/2006 |

OTHER PUBLICATIONS

Hegeman et al; U.S. Appl. No. 11/787,543 entitled "Tool with articulation lock," filed Apr. 16, 2007.

Hinman, Cameron; U.S. Appl. No. 11/787,607 entitled "Tool with rotation lock," filed Apr. 16, 2007.

Hinman, Cameron; U.S. Appl. No. 11/787,605 entitled "Tool with multi-state ratcheted end effector," filed Apr. 16, 2007.

Hinman et al; U.S. Appl. No. 11/787,599 entitled "Tool with end effector force limiter," filed Apr. 16, 2007.

Danitz et al.; U.S. Appl. No. 12/109,333 entitled "Articulating instrument," filed Apr. 24, 2008.

Isbell Jr., Lewis; U.S. Appl. No. 12/542,589 entitled "Instrument with articulation lock," filed Aug. 17, 2009.

Hinman, Cameron; U.S. Appl. No. 12/508,478 entitled "Articulating mechanism," filed Jul. 23, 2009.

Danitz et al.; U.S. Appl. No. 12/766,818 entitled "Articulating instruments with joystick control," filed Apr. 23, 2010.

Danitz, David J.; U.S. Appl. No. 12/766,820 entitled "Articulating mechanism with bifurcating control," filed Apr. 23, 2010.

Danitz, David J.; U.S. Appl. No. 12/766,822 entitled "Articulating catheters," filed Apr. 23, 2010.

Danitz, David J.; U.S. Appl. No. 12/766,825 entitled "Articulating endoscopes," filed Apr. 23, 2010.

Danitz, David J.; U.S. Appl. No. 12/766,827 entitled "Articulating retractors," filed Apr. 23, 2010.

Cox, James; The minimally invasive Maze-III procedure; Operative Techniques in Thoracic and Cardiovascular Surgery; vol. 5; No. 1; pp. 79-92; Feb. 2000.

Simha et al.; The elctrocautery maze—how I do it; The Heart Surgery Forum; vol. 4; No. 4; pp. 340-345; Aug. 23, 2001.

Prasad et al.; Epicardial ablation on the beating heart: progress towards an off-pump maze procedure; The Heart Surgery Forum; vol. 5/ No. 2; pp. 100-104; Jun. 27, 2001.

* cited by examiner

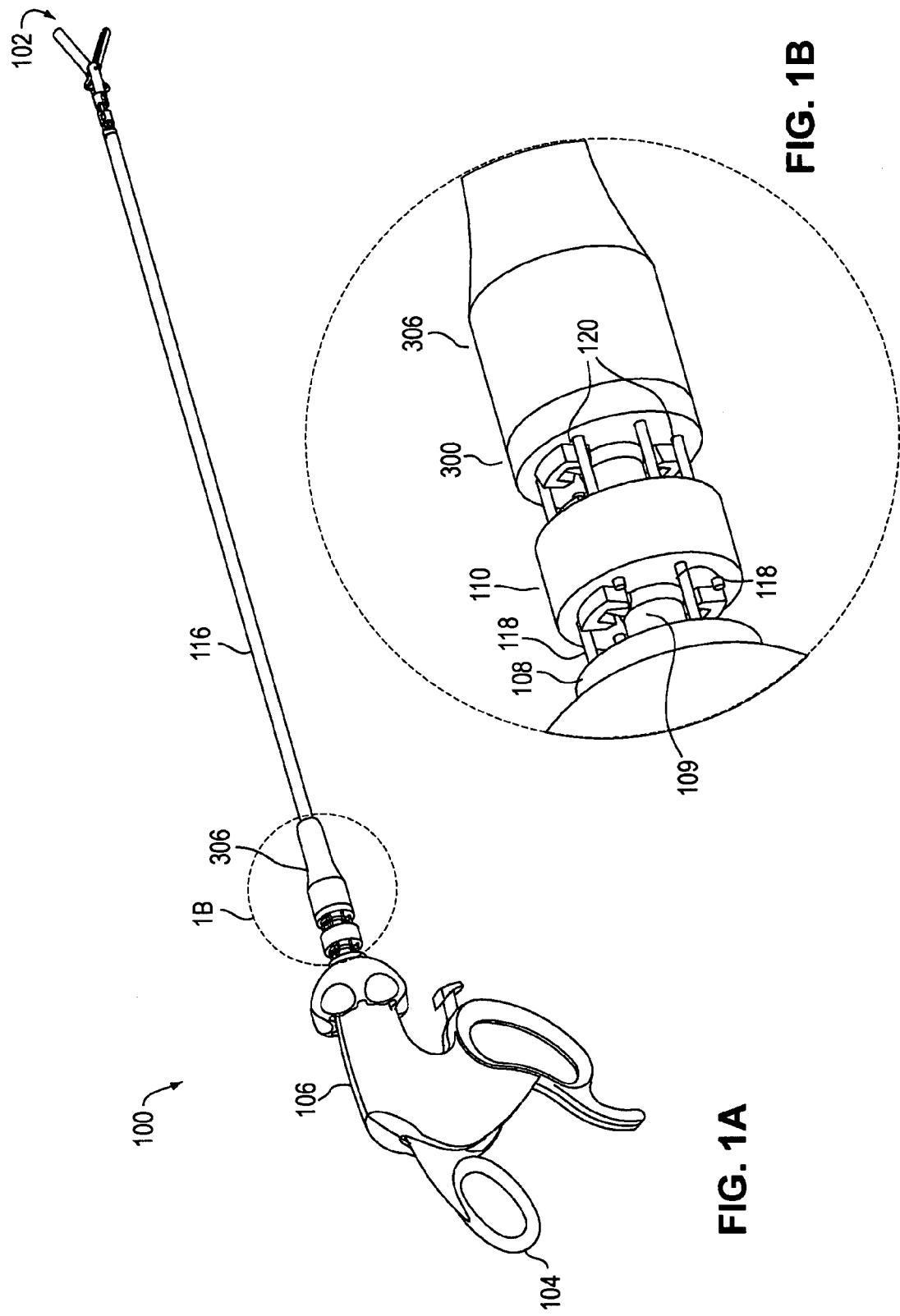

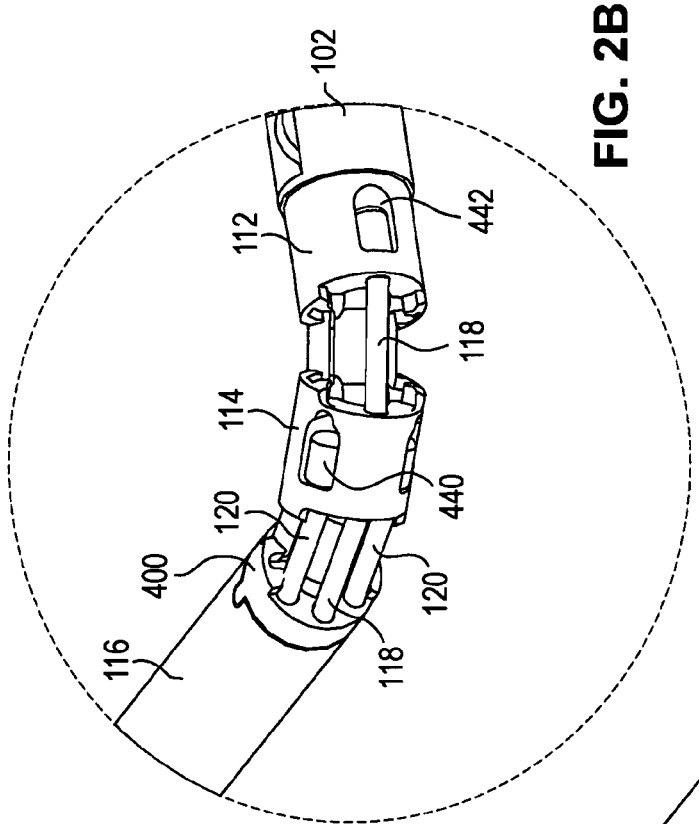
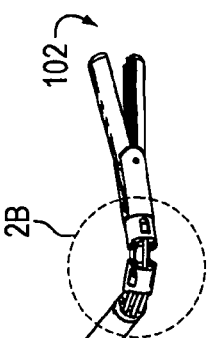
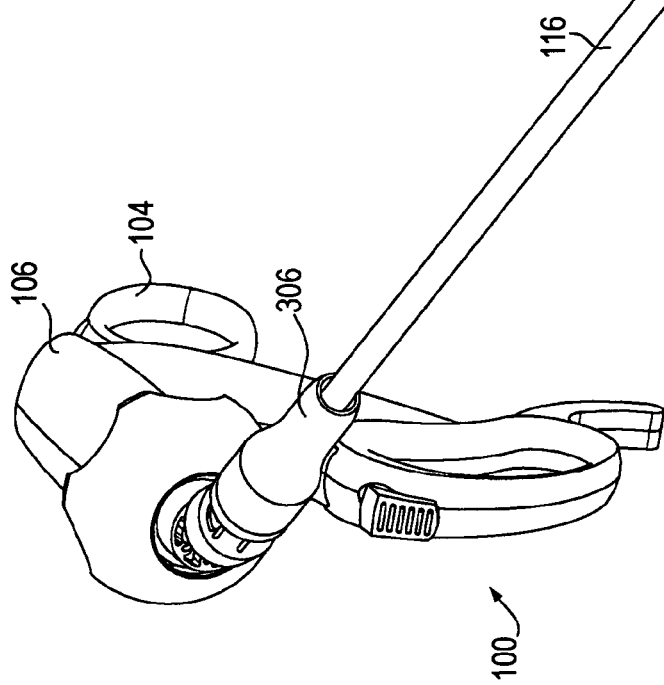
FIG. 2B
FIG. 2A

ARTICULATING TOOL WITH IMPROVED TENSION MEMBER SYSTEM

CROSS REFERENCE TO RELATED APPLICATIONS

This application is related to the following concurrently filed US patent applications: "Tool with articulation lock" of Hegeman, Danitz, Hinman, and Alvord, "Tool with force limiter" of Hinman and Bertsch, "Tool with multi-state ratcheted end effector" of Hinman, and "Tool with rotation lock" of Hinman and Danitz.

INCORPORATION BY REFERENCE

All publications and patent applications mentioned in this specification are herein incorporated by reference to the same extent as if each individual publication or patent application was specifically and individually indicated to be incorporated by reference.

FIELD OF THE INVENTION

This invention relates to articulating mechanisms and applications thereof, including the remote guidance and manipulation of surgical or diagnostic tools.

BACKGROUND OF THE INVENTION

Surgical procedures such as endoscopy and laparoscopy typically employ instruments that are steered within or towards a target organ or tissue from a position outside the body. Examples of endoscopic procedures include sigmoidoscopy, colonoscopy, esophagogastroduodenoscopy, and bronchoscopy, as well as newer procedures in natural orifice transluminal endoscopic surgery ("NOTES"). Traditionally, the insertion tube of an endoscope is advanced by pushing it forward, and retracted by pulling it back. The tip of the tube may be directed by twisting and general up/down and left/right movements. Oftentimes, this limited range of motion makes it difficult to negotiate acute angles (e.g., in the rectosigmoid colon), creating patient discomfort and increasing the risk of trauma to surrounding tissues.

Laparoscopy involves the placement of trocar ports according to anatomical landmarks. The number of ports usually varies with the intended procedure and number of instruments required to obtain satisfactory tissue mobilization and exposure of the operative field. Although there are many benefits of laparoscopic surgery, e.g., less postoperative pain, early mobilization, and decreased adhesion formation, it is often difficult to achieve optimal retraction of organs and maneuverability of conventional instruments through laparoscopic ports. In some cases, these deficiencies may lead to increased operative time or imprecise placement of components such as staples and sutures.

Steerable catheters are also well known for both diagnostic and therapeutic applications. Similar to endoscopes, such catheters include tips that can be directed in generally limited ranges of motion to navigate a patient's vasculature. There have been many attempts to design endoscopes and catheters with improved steerability. For example, U.S. Pat. No. 3,557,780 to Sato; U.S. Pat. No. 5,271,381 to Ailinger et al.; U.S. Pat. No. 5,916,146 to Alotta et al.; U.S. Pat. No. 6,270,453 to Sakai, and U.S. Pat. No. 7,147,650 to Lee describe endoscopic instruments with one or more flexible portions that may be bent by actuation of a single set of wires. The wires are actuated from the proximal end of the instrument by rotating pinions (Sato), manipulating knobs (Ailinger et al.), a steerable arm (Alotta et al.), by a pulley mechanism (Sato), or by manipulation of complementary portions (Lee). U.S. Pat. No. 5,916,147 to Boury et al. discloses a steerable catheter having four wires that run within the catheter wall. Each wire terminates at a different part of the catheter. The proximal ends of the wires extend loosely from the catheter so that the physician may pull them. The physician is able to shape and thereby steer the catheter by selectively placing the wires under tension.

Recently, surgical instruments, including minimally invasive surgical instruments, have been developed that are more ergonomic and which have a wider range of motion and more precise control of movement. These instruments may include mechanisms that articulate using a series of links coupled with one or more sets of tension bearing members, such as cables. As with conventional instruments used in minimally invasive surgery, rotation of the shaft and end effector with respect to the handle is also an important feature of cable and link type instruments to aid with dissecting, suturing, retracting, knot tying, etc. With increasing complexity in the cable systems comes the possibility of undesirable interaction among cables within portions of the tool. Further associated with complexity involving the cables comes an increasing level of complexity, delicacy, and tedium in the manufacture of these instruments. To address such issues, further improvements in the features and design of surgical instruments are desirable.

SUMMARY OF THE INVENTION

The invention provides an articulating tool with an improved tension member design as well as methods of assembling such tools. The articulating tool is appropriate for multiple uses, including medical uses such as diagnostic and surgical uses. Embodiments of the articulating tool include a shaft having a proximal and a distal end, an articulation mechanism, and an elongated guide located along at least a portion of the shaft, the guide being configured to guide the tension bearing members. The articulation mechanism includes a movable proximal element disposed at the proximal end of the shaft, a movable distal element disposed at the distal end of the shaft, and a plurality of tension bearing members extending between the proximal and distal elements such that movement of the movable proximal element with respect to the shaft causes a corresponding movement of the movable distal element with respect to the shaft.

Embodiments of the guide include a plurality of channels extending along its length, each channel for receiving one of the plurality of tension bearing members. In some embodiments the channels are circumferentially closed; in other embodiments the channels are grooves. Embodiments of the channels include those that form a generally straight path, and those that form a generally helical path. Embodiments that form a helical path may revolve about 180 degrees.

The guide may be generally circular in cross section with the channels spaced around the circumference of the cross section. Some embodiments of the guide are configured to guide at least three tension bearing members; others are configured to guide at least six tension bearing members. The guide may further include a central channel for receiving a tension bearing member in addition to the aforementioned plurality. In some embodiments there may be two or more such central channels, the channels for receiving operable elements of the tool. Exemplary operable elements in addition to tension-bearing and compression-bearing members, may include elements such as wires, optical fibers, and hydraulic or vacuum tubes.

In some embodiments of the tool, the tension bearing members are also compression bearing members. In some embodiments of the tool, the shaft includes a tube, wherein the elongated guide has a length and a constant cross section along substantially its entire length, and wherein the guide element is located within the tube. In some embodiments of the tool, the elongated guide element is made of a flexible polymer. And in some embodiments, both the shaft and the guide are flexible.

Embodiments of the tool include a fixed attachment between the movable proximal element and the proximal end of tension bearing members. In some embodiments of the tool, fixed attachment comprises a crimp in the movable proximal element; in other embodiments, the fixed attachment comprises an ultrasonic weld in the movable proximal element.

In some embodiments of the tool, an end cap for guiding the plurality of tension bearing members is disposed at least one end of the shaft. In some of these embodiments, the shaft itself includes the end cap. In some of these embodiments, the end cap guides each of the tension bearing members from a first radial distance to a second radial distance from a central axis. And in some of these embodiments, end cap is located adjacent to a proximal end of the shaft, and the first and second radial distances differ by a factor of about three. In some of the tool embodiments with an end cap, the end cap and the elongated guide have inter-engaging rotational alignment features.

Embodiments of the invention also include a method of assembling the above summarized tool with an elongated guide. The method includes inserting the elongated guide into a lumen of the shaft element, attaching the end cap to an end of the lumen, and inserting at least one of the tension bearing members through the end cap and the guide.

This method may further include rotating at least one end of the guide around a longitudinal axis relative to an opposite end of the guide, and fixing the relative positions of the rotated ends. Embodiments of this method include a step order in which the inserting step is performed before the rotating step, as well as an order in which the rotating step is performed before the inserting step.

The method may further include deforming the movable proximal element so as to attach the proximal element and the proximal end of the tension bearing element together. And it may also include deforming the movable distal element so as to attach the distal element and the distal end of the tension bearing element together.

Embodiments of the invention also include an articulating tool having a distal portion and a proximal portion as well as an articulation mechanism for manipulating angular orientation of the distal portion. The articulation mechanism includes a pair of links, the pair including a proximal link on the proximal portion of the tool and a distal link on the distal portion of the tool. The mechanism further includes a plurality of tension bearing members interconnecting the proximal and distal links such that movement of the proximal link causes corresponding relative movement of the distal link through the tension bearing members. In these embodiments, a portion of one of the links adjacent to a tension bearing member is deformed against the member, thereby fixedly attaching the member and the link together.

In some of these embodiments, the link portion is deformed by a crimping process. In other embodiments, the link is formed of plastic and the link portion has been deformed by an ultrasonic welding process. In some embodiments, both of the proximal and distal links include a portion deformed against a tension bearing member. In other embodiments, one link of the pair of links includes a portion deformed against a tension bearing member and the other link includes a pocket for receiving an enlarged portion of the tension bearing member. In some of these embodiments, one link of the pair of links includes at least three of the deformed portions and the other link includes at least three of the pockets. In some of these embodiments, the pocket on the other link is located on a peripheral edge of that link. In other embodiments, the enlarged portion of the tension bearing member may only enter the pocket from a radial direction.

Some embodiments of the tool include at least two pairs of links, and the tool may also include at least three tension bearing members interconnecting each pair of links. In some embodiments of the tool, the tension bearing members are also compression bearing members.

Some embodiments of the articulating tool include an end effector disposed at a distal portion of the tool, a handle at a proximal portion of the tool, a shaft element supporting the end effector, an articulation mechanism for manipulating angular orientation of the end effector with respect to the shaft, and a guide element configured to guide the tension bearing members. The articulation mechanism of this embodiment includes a plurality of tension bearing members.

Some embodiments of the articulating tool include an end effector disposed at a distal portion of the tool, a handle at a proximal portion of the tool, a shaft element supporting the end effector, an articulation mechanism for manipulating angular orientation of the end effector with respect to the shaft, and a guide element configured to guide the tension bearing members. The articulation mechanism of this embodiment includes a plurality of tension bearing members. In some of these embodiments, there is a connection between each member of the plurality of tension bearing members and a distal link, the link configured to manipulate or contribute to the manipulation of the angular orientation of the end effector. In some of these embodiments, the connection is formed by a crimp of the distal link against the member; in other embodiments the connection is formed by an ultrasonic weld of the distal link and the member.

Some embodiments of the tool include a shaft with a proximal and a distal end, an articulation mechanism, and a plurality of channels extending the length of the shaft between the proximal and distal end. The articulation mechanism includes a movable proximal element at the proximal end of the shaft and a movable distal element at the distal end of the shaft, and a plurality of tension bearing members extending between the proximal and distal elements so that movement of the proximal element with respect to the shaft causes a corresponding movement of the distal element with respect to the shaft. In these embodiments, each channel of the plurality of channels is configured to guide one of the plurality of tension bearing members along the shaft. The channels are disposed at a radial distance from the central axis of the shaft, and in some of these embodiments the radial distance is variable along the length of the shaft.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings which are briefly described below.

FIG. 1A is an obliquely distal-looking perspective view of an exemplary articulating device having a handle and an end effector. FIG. 1B is a detailed view of the circled portion of FIG. 1A, which includes proximal links and an end-cap housing cover of a tension bearing member guide.

FIG. 2 shows the device of FIG. 1 in a proximal-looking view, with the handle and end effector in an articulated position. FIG. 2B is a detailed view of the circled portion of FIG. 2A, which includes distal links and distal end-cap housing cover of a tension bearing member guide.

DETAILED DESCRIPTION OF THE INVENTION

Figure 3:
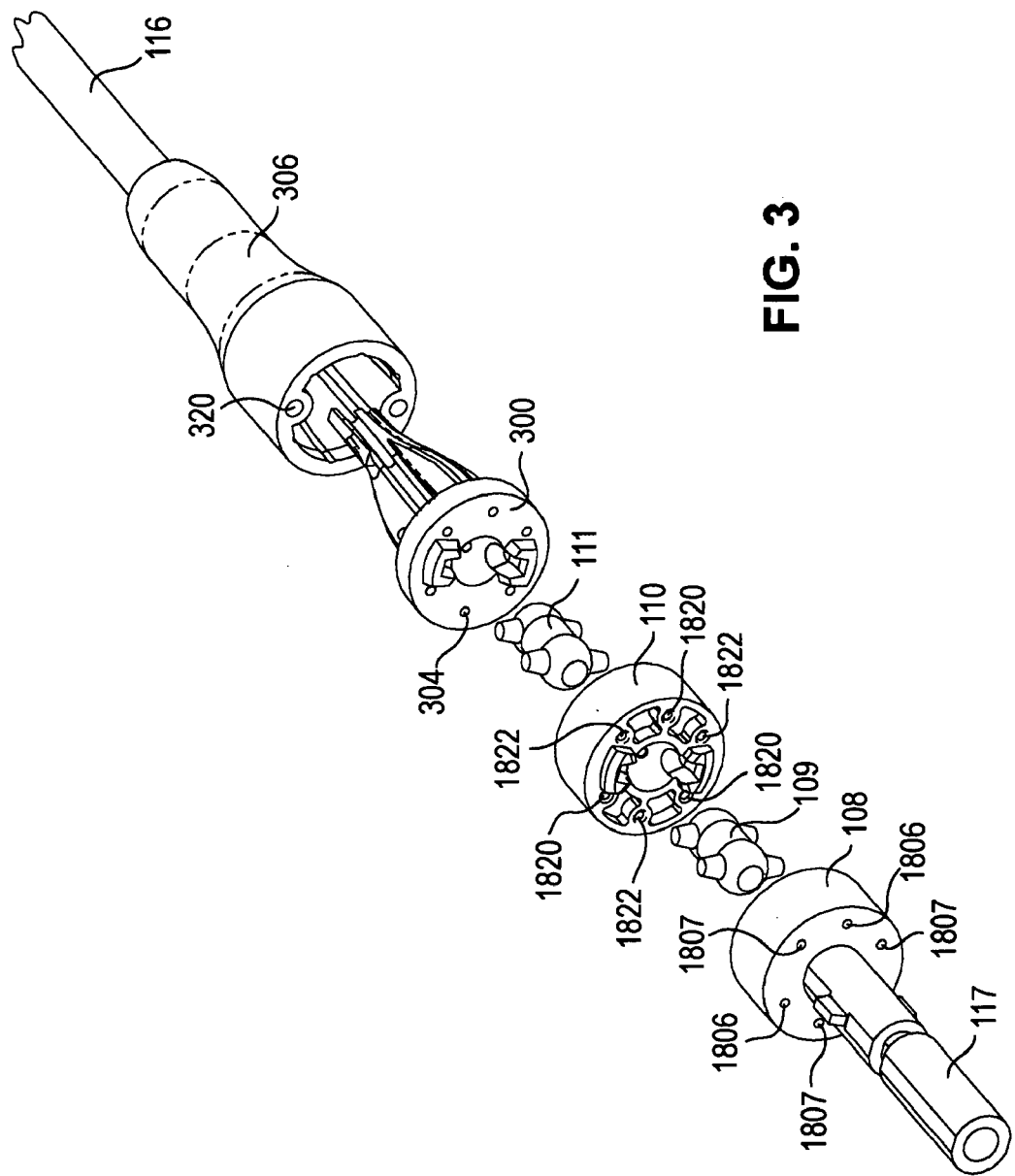
FIG. 3 is an exploded perspective view of certain proximal components of the articulating device.

Articulating tools are described in U.S. Pat. No. 7,090,637; US 2005/0107667; US 2005/0273084; US 2005/0273085; US 2006/0111209, US 2006/0111210, and US 2006/0111615. The articulating mechanisms of the tools described in those publications use multiple pairs of segments or links controlled, e.g., by multiple sets of cables, as well as tools that have a single pair of links, connected by a single set of cables, such as those described in U.S. Pat. No. 5,916,146. Depending upon the specific design of the device, the links can be discrete segments (as described, e.g., in U.S. Pat. No. 7,090,637) or discrete portions of a flexible segment (as described, e.g., in US 2005/0273085). The instrument may also include steerable or controllable links, e.g., as described in US 2005/0273084, US 2006/0111209 and US 2006/0111210. Embodiments of the invention are not specific to any particular type of link, and may include any type of link known in the art. The devices of this invention may include optional end effectors at their distal ends and end effector actuators supported by a handle at their proximal ends. When using such articulating instruments, a user may manipulate the proximal end of the instrument, thereby moving one or more distal links of the articulation mechanism.

FIGS. 1A and 2A show an articulatable tool 100 with an end effector 102 at its distal end and an end effector actuator 104 within a handle 106 at its proximal end: FIG. 1A shows the tool in a neutral or non-articulated configuration, while FIG. 2A shows the tool in an articulated position or configuration. FIG. 1B shows detail (encircled in FIG. 1A) of the proximal links of the tool and the proximal end-cap cover of a tension bearing member guide system. FIG. 2B shows detail (encircled in FIG. 2A) of the distal links of the tool and the distal end-cap cover of a tension bearing member guide system. Instrument 100 may be used, e.g., in a laparoscopic procedure requiring grasping or cutting within a patient. Exemplary embodiments of the tool 100 may also be useful in endoscopic procedures, particularly when, as in some embodiments, the tool has a flexible shaft. Still other embodiments may be used for percutaneous procedures, such as a catheter. Still other embodiments include devices that are directed toward natural orifice transluminal endoscopic surgery ("NOTES"). Embodiments of the invention may include a wide variety of tools, some with medical or diagnostic purposes, and others that are applied to other types of tasks where the articulational capabilities of the tool provide benefit.

Proximal articulation links 108 and 110 extend distally from handle 106, and distal articulation links 112 and 114 extend proximally from end effector 102. Proximal link 108 is a spindle and is connected to and moves with handle 106. Likewise, distal link 112 is connected to and moves with end effector 102. An elongated shaft 116 is disposed between the proximal links and the distal links; in some embodiments the shaft is rigid, in other embodiments the shaft may be flexible.

A set of tension bearing elements or control cables 118 is attached to proximal link 108, extends through proximal link 110, shaft 116 and distal link 114 and is attached to distal link 112, as shown in FIGS. 1A and 1B. A second set of tension bearing element or control cables 120 is attached to proximal link 110, extends through shaft 116 and is attached to distal link 114. In this embodiment, there are three control cables 118 in the first set and three control cables 120 in the second set. It should be appreciated, however, that other numbers of control cables may be used to connect corresponding proximal and distal links. In addition, tension bearing elements other than cables may be used to connect corresponding links.

As shown in FIGS. 1A, 1B, 2A, and 2B, movement of handle 106 and proximal link 108 with respect to proximal link 110 moves end effector 102 and distal link 112 in a relative and corresponding manner. Likewise, movement of proximal link 110 with respect to shaft 116 moves distal link 114 with respect to shaft 116 in a relative and corresponding manner, also as shown in FIG. 2. This relative articulation movement provides a way for a user to remotely manipulate the end effector through movement of the handle. It should be understood that the proximal and distal links can be connected by the tension bearing elements so as to move in the same direction with respect to the shaft (thereby providing a mirror image movement) or in opposite directions with respect to the shaft, depending on whether the tension bearing elements connect the corresponding links on the opposite sides or on the same sides of the links, respectively. In addition, the degree of relative movement can be determined by the relative diameters of the cables' connections to corresponding links as well as through the use and specific design of bushings or spacer links separating the connected proximal and distal links. For example, in the embodiment shown in FIGS. 1-20, the cables' radial spacing on the proximal links is about three times greater than their radial spacing on the distal links. This means that a movement of about 5° in a proximal link will cause a corresponding movement of about 15° in a distal link. Further details of these links are provided in US2005/0273085, which is hereby incorporated by this reference.

In the embodiment illustrated in FIG. 1, the end effector 102 is a pair of jaws. Actuation force is transmitted from end effector actuator 104 through a transmission that includes a linearly movable rod and a rotatable rod actuator (not shown). Other end effectors (surgical, diagnostic, etc.) and end effector actuators may be used with the articulating tool of this invention. In some embodiments, the distal links, themselves, can comprise an end effector, such as, for example, a retractor. The movable rod may comprise any flexible material; in some embodiments Nitinol offers particular advantages as it is sufficiently flexible to accommodate articulation, and yet can still carry a compressive load sufficiently, for example, to be able to push open an end effector, such as a set of jaws. In some embodiments, a series of proximal links, themselves, can comprise a "handle" with no other rigid handle being provided. In other words, the proximal links may be formed into a particular shape which is emulated by a corresponding series of distal links. More details of such embodiments are provided in U.S. Pat. No. 7,090,637.

FIG. 3 shows an exploded view of certain proximal components of the articulating tool. The tension bearing elements have been omitted for clarity. As shown, a double headed bushing 109 is disposed between links 108 and 110, and another bushing 111 is disposed between links 110 and a proximal end cap 300. The interaction of bushings 109 and 111 with links 108 and 110 and with proximal end cap 300 is described in more detail in U.S. 2005/0273084, U.S. 2006/0111209, and U.S. 2006/0111210. If the tension bearing cables 118 and 120 were shown in FIG. 3 as they are in FIGS. 1 and 2, the proximal ends of the three cables 118 would terminate in openings 1806 of link 108, and the cables would pass through openings 1820 in link 110 and openings 304 in end cap 300 before entering shaft 116. Likewise, the proximal ends of three cables 120 would terminate in openings 1822 of link 110 and would pass through openings 304 in proximal end cap 300 before entering shaft 116. A tapered end cap housing or cover 306 is rigidly fixed to shaft 116 and provides a transition from end cap 300 to shaft 116.

Figure 5:
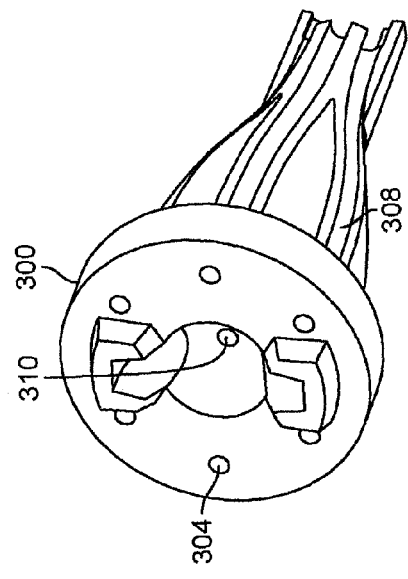
FIGS. 4-6 show details of an end cap for use with the articulating device.
Figure 6:
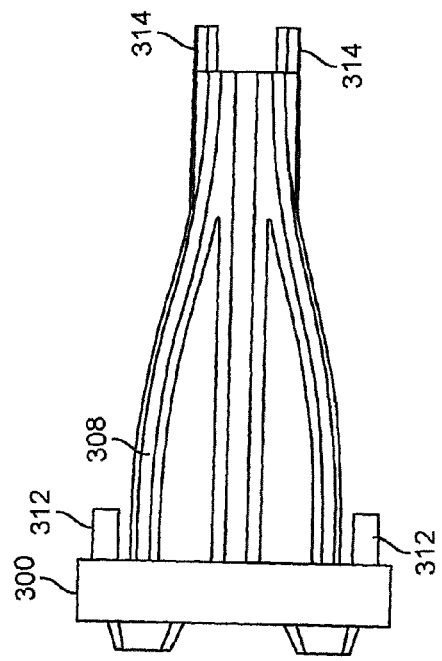
Figure 4:
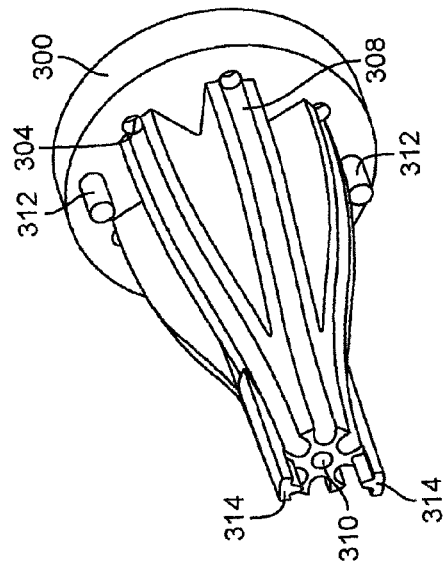

FIGS. 4-6 show details of end cap 300. Cable openings 304 lead to channels 308 extending distally from the end cap proximal face. Channels 308 taper the radial distance between the cables within the proximal links 108 and 110 to a radial distribution suitable for the diameter of shaft 116. Channels 308 depicted are in the form of grooves. In other embodiments (not shown) channels may be in a circumferentially enclosed form. An opening 310 is provided for passage of the end effector actuation rod. A pair of pins 312 connect the end cap 300 to the end cap housing, as explained below. A pair of tines 314 connect with a shaft cable guide, as is also explained below.

Figure 8:
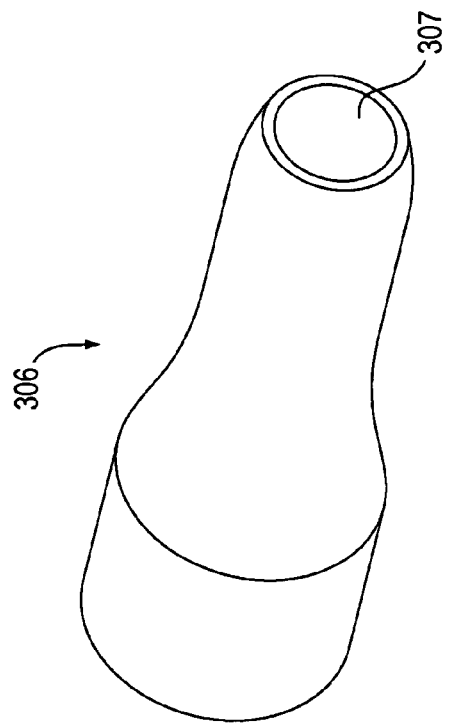
FIGS. 7-9 show details of a proximal end cap housing for use with the articulating device.
Figure 7:
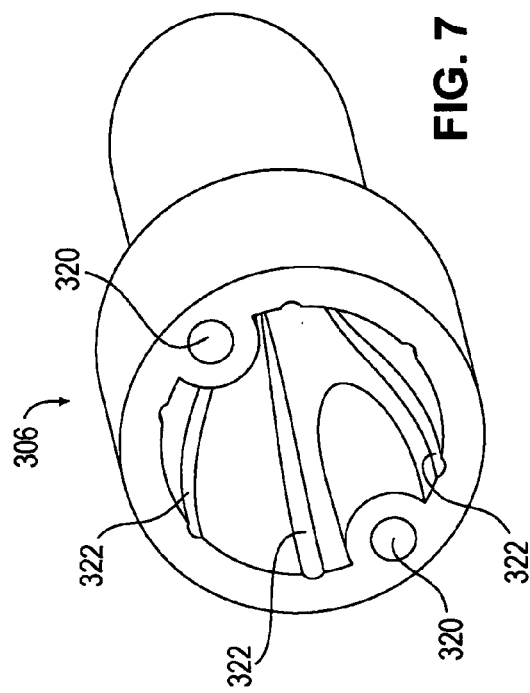
Figure 9:
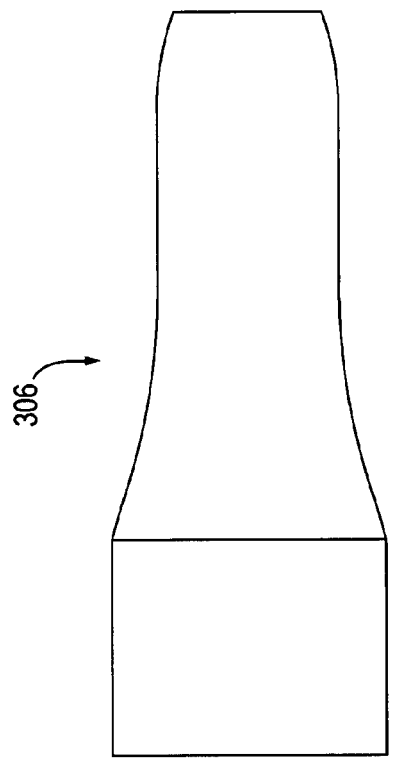
Figure 18:
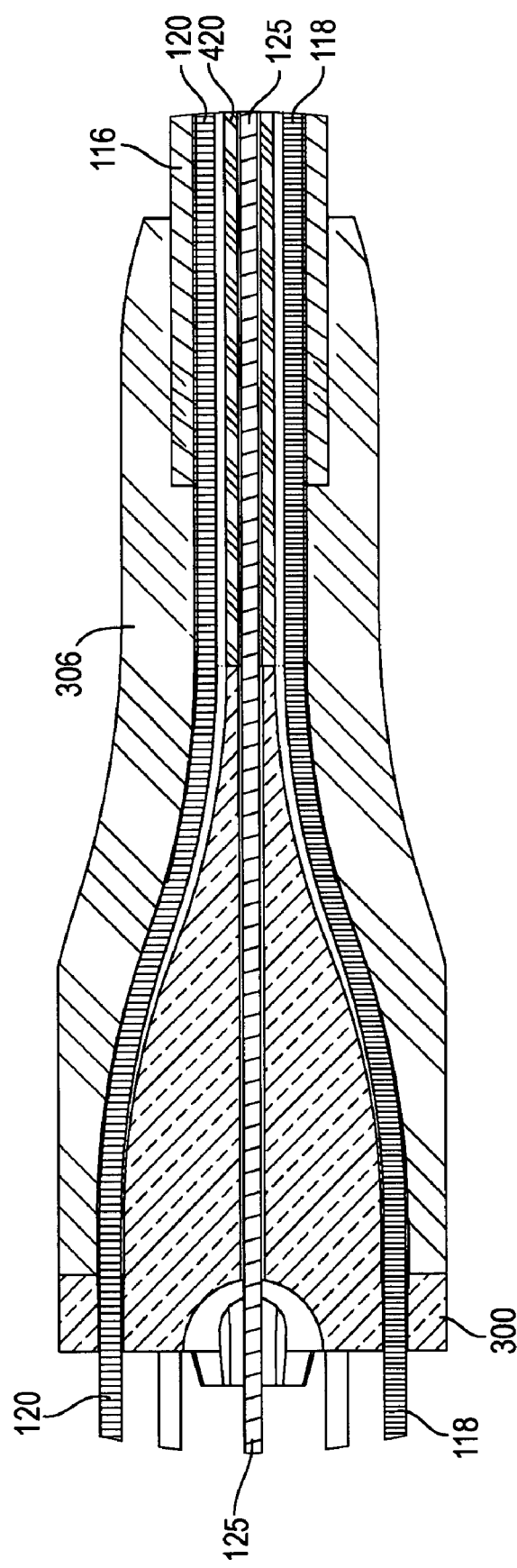
FIG. 18 is a cross-sectional view showing proximal elements of the articulating device.
Figure 19:
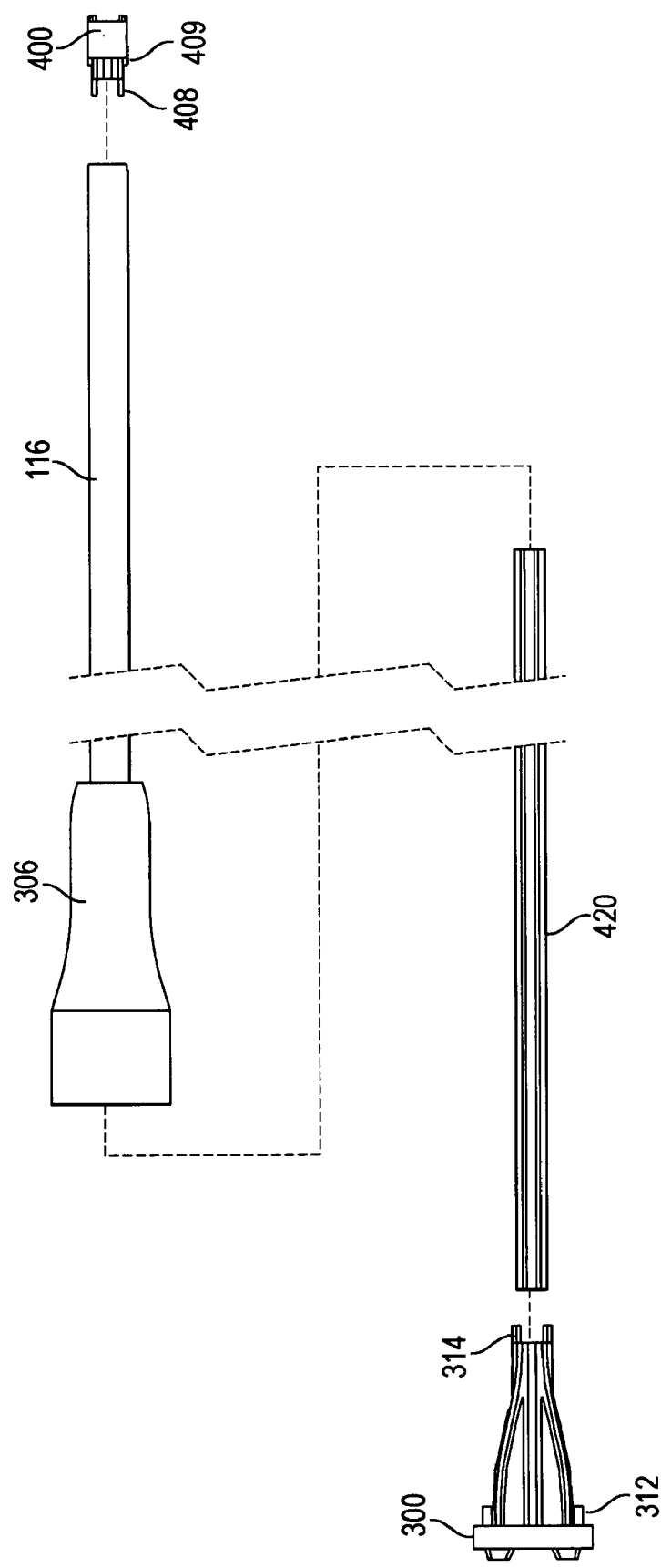
FIG. 19 is a partial exploded view of the articulating device shown in FIGS. 1-18.

FIGS. 7-9 show details of the end cap housing 306. A pair of holes 320 mate with the pins 312 of end cap 300. Channels 322 may be formed on the inner surface of housing 306. These channels 322 line up with channels 308 of end cap 300 to help guide the cables as they transition from the proximal links into the shaft. A stepped distal opening 307 surrounds the proximal end of the shaft 116 (as shown in FIG. 18). The proximal end cap 300 and end cap housing 306 cooperate to provide a smooth transition between the cables' radial distribution within the shaft and their radial distribution on the proximal links. As shown in FIG. 18, cables 118 and 120 are constrained by the cooperating channels of end cap 300 and end cap housing 306 to limit any lateral movement of the cables.

Figure 11:
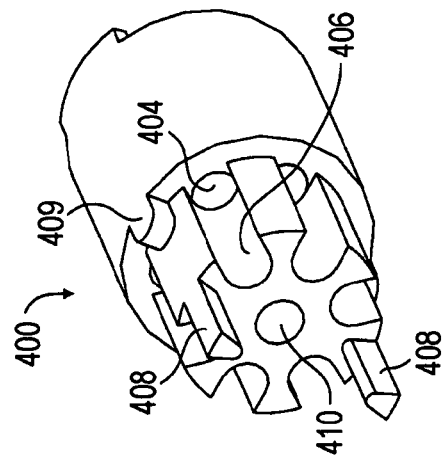
FIGS. 10-12 show details of a distal end cap for use with the articulating device.
Figure 10:
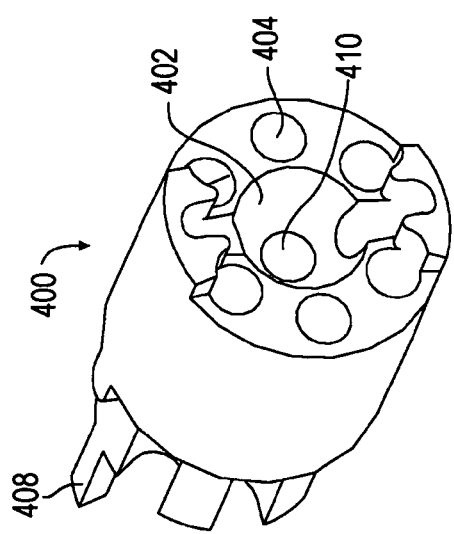
Figure 12:
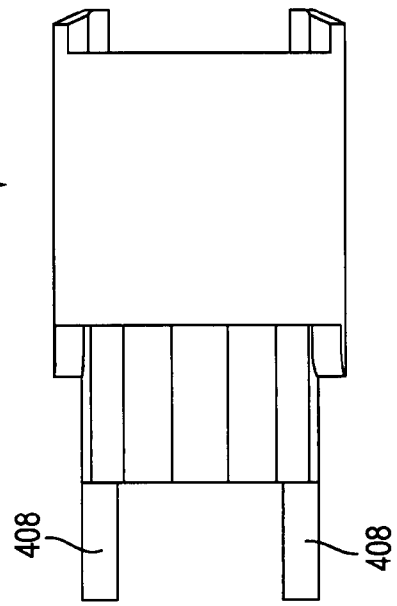

FIGS. 10-12 show details of a distal end cap 400. Like the proximal end cap, distal end cap 400 cooperates with a link bushing in the articulation mechanism and therefore has a socket 402 on its distal face and other features to interface with a bushing. Openings 404 line up with channels 406 to guide the tension bearing cables to the distal links. A pair of tines 408 connect with the shaft cable guide, and a tab 409 indexes end cap 400 with the shaft. An opening 410 permits passage of the end effector actuation rod.

Some embodiments of the invention have a tension bearing element guide extending along part or all of the shaft. One purpose of this guide is to maintain the relative position and orientation of the cables or other tension bearing members within the shaft. The guide also aids in the initial assembly of the tool, as discussed below.

Figure 13B:
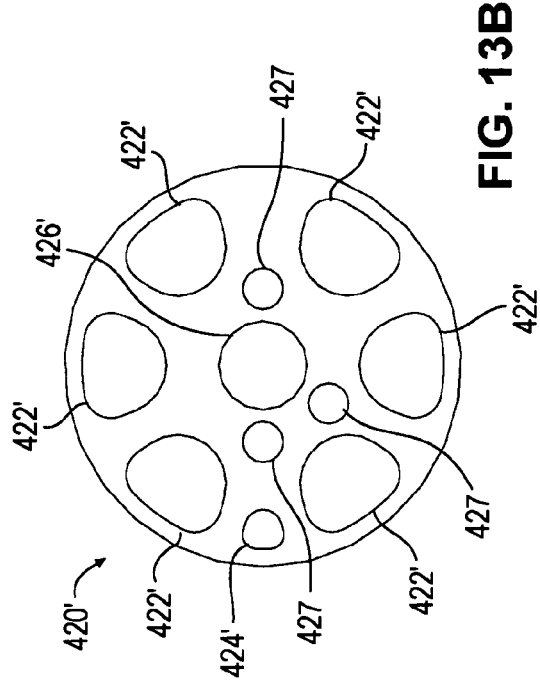
FIG. 13B is an end view of an alternative embodiment tension bearing element guide.
Figure 13A:
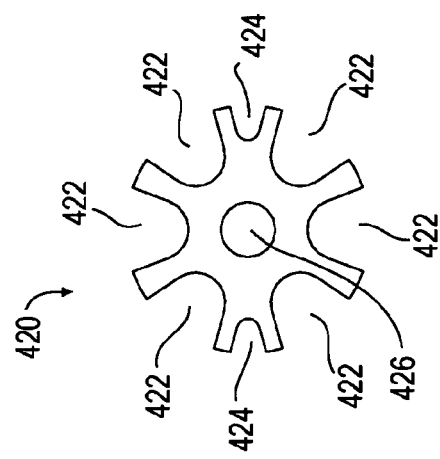
FIG. 13A is an end view of a tension bearing element guide for use with an articulating device.
Figure 14:
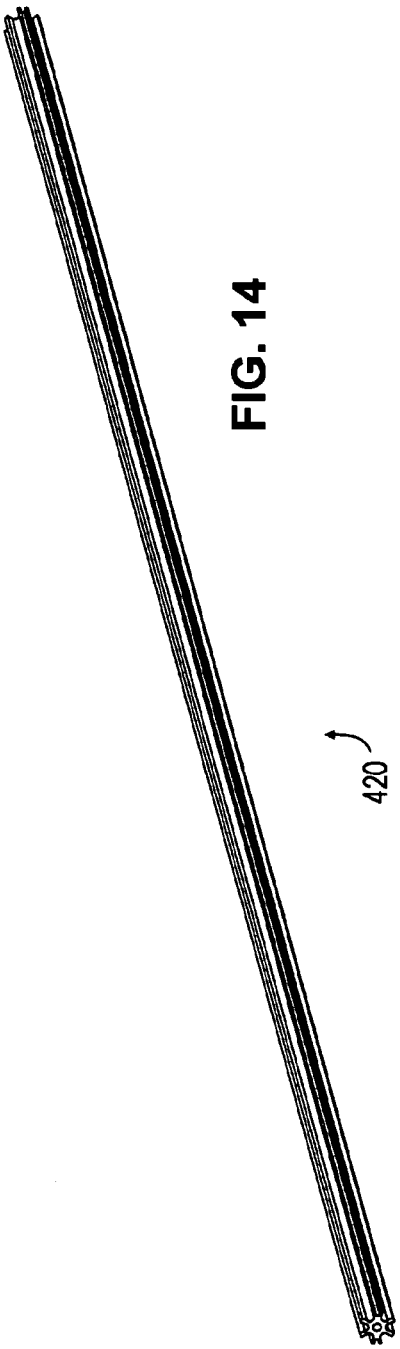
FIG. 14 is a perspective view of the tension bearing element guide of FIG. 13.
Figure 16:
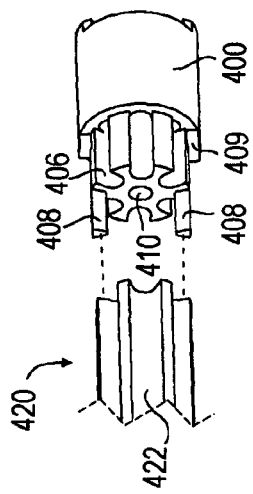
FIG. 16 is a partial exploded view of the distal end cap of FIGS. 10-12 and the tension bearing element guide of FIG. 13.
Figure 15:
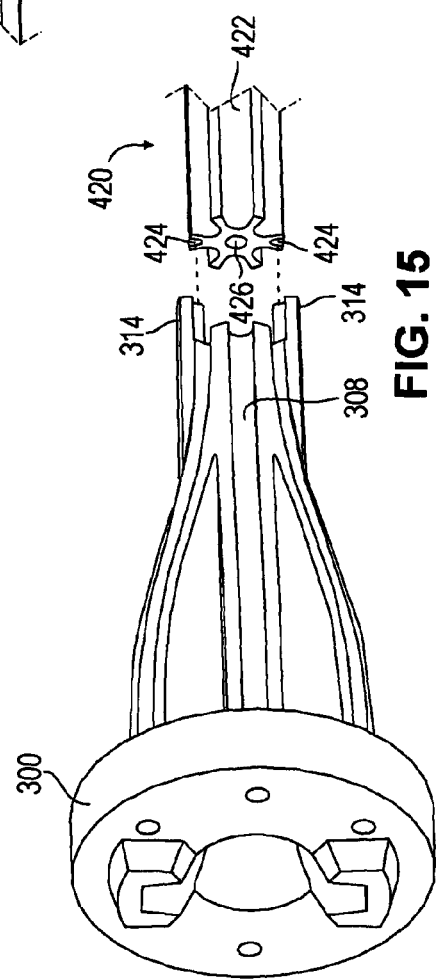
FIG. 15 is a partial exploded view of the proximal end cap of FIGS. 7-9 and the tension bearing element guide of FIG. 13.

FIGS. 13-19 show one embodiment of a shaft cable guide 420 and its interaction with proximal end cap 300 and distal end cap 400. Guide 420 has channels 422 in which the cables 118 and 120 or other tension bearing elements or elements may be disposed. Channels 422 depicted are in the form of grooves. In other embodiments (FIG. 13B) channels may be in a circumferentially enclosed form. In this embodiment, the proximal ends of channels 422 line up with channels 308 in proximal end cap 300 (as shown in FIG. 15) and the distal ends of channels 422 line up with channels 406 in distal end cap 400 (as shown in FIG. 16). To help with alignment, tines 314 of proximal end cap 300 can mate with the proximal ends of alignment channels 424 in guide 420 (as shown in FIG. 15), and tines 408 of distal end cap 400 can mate with the distal ends of alignment channels 424 (as shown in FIG. 16).

Some embodiments may include a central channel or lumen 426 in guide 420 (FIG. 13A) that permits passage of an operable element such as the articulating tool's movable actuation rod 125 (as shown in FIG. 18), which further functions to prevent buckling of the actuation rod during its movement. The rod 125, in some embodiments, in addition to being a tension bearing member may further be a compression bearing member. Central channel or lumen 426 should be understood as being generally centrally-located, the channel need not be dead centrally located, and may be off-center. In some embodiments the guide may include one or more additional channels or lumina 426' and 427, as seen in FIG. 13B, with four exemplary channels. These channels 426' and 427 are generally centrally-disposed, in contrast to the more circumferentially disposed channels 422 or 422'. Such separate channels 426' and 427, in addition to accommodating movable actuation rod 125, may further accommodate other operable elements or components such as any type of tension bearing member or compression bearing member, wires, cables, hydraulic lines, vacuum lines, optical fibers, or any element useful in the operation of the distal portion of the tool. Separation of the central lumen into separate lumina provides for segregation of components or elements contained therein, and may facilitate the assembly of the tool, or the independence of the operation of the elements contained therein. As seen in FIG. 13B, tension member channels 422' and alignment channel 424' may have a closed configuration. Guide 420' of FIG. 13B may be used within a shaft tube as described below. Alternatively, in some embodiments, guide 420' may itself serve as a shaft.

Figure 17:
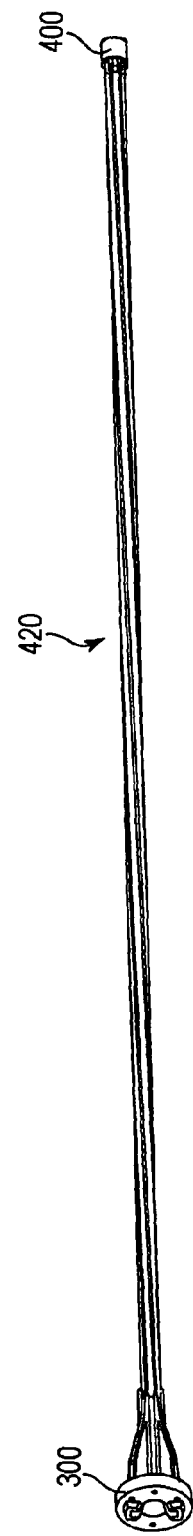
FIG. 17 is a perspective view showing the tension bearing element guide twisted 180°.

In the orientation shown in FIG. 14, tension member guide 420 guides the cables or other tension bearing members axially along the shaft so that the cables' entry and exit points are at the same circumferential positions about the circumference of the shaft to provide movement of distal links that is opposite to the movement of their corresponding proximal links. For example, in this orientation of the guide 420, movement of a proximal link to the right of the shaft will cause movement of the corresponding distal link to the left of the shaft. To provide mirrored movement of proximal and distal links, the cables or other tension bearing elements must connect to the distal links at positions 180° opposite to their circumferential connection position on the corresponding proximal links. To accomplish this shift in circumferential position without entanglement of the cables, guide 420 may be twisted 180° from proximal to distal end, as shown in FIG. 17. It should be understood that guide 420 may also be twisted more or less than 180°, as desired.

In one embodiment, guide 420 may be made of plastic through an extrusion process. The guide can be formed with any desired amount axial twist, a twist of about 180° being typical, or the twist can be added during the assembly process, as described below. Further, other types of manufacturing processes known in the art may be used to form the guide, and in some embodiments it may be desirable to assemble multiple components into a whole to form the guide.

A variety of protocols and procedural steps may be used to assemble an articulating tool with embodiments of the tension member guide. The following procedure is provided merely by way of example. When assembling the articulating tool of the embodiment shown, the proximal end cap housing 306 may be rigidly attached to shaft 116. The proximal end cap 300 may also be rigidly attached to the proximal end of guide 420 by pressing tines 314 into the corresponding channels 424 in the guide and then gluing, if necessary. The proximal end cap/guide subassembly may then be inserted into the proximal end of end cap housing 306, as suggested by FIG. 19, by inserting pins 312 into holes 320 in the end cap housing. The tines 408 of distal end cap 400 may then be inserted into the distal ends of guide channels 424. Distal end cap 400 and the distal end of guide 424 may then be twisted 180° (or any other angle), if desired, before attaching by inserting tabs 409 into corresponding slots in the distal end of shaft 116. As mentioned above, other variations on assembly can by recognized by those practiced in manufacturing arts. Briefly, for example, the guide 420 could be fixed to proximal end cap 300, or guide 420 could be fixed to distal end cap 440, or guide 420 could be inserted into the shaft 116 and then end caps fixed thereto, or tension members or cables could be first inserted into the guide, and the guide thence into the shaft. After assembly of the shaft, end cap housing, end caps, and tension bearing element guide, the cables and links may be assembled.

Figure 20:
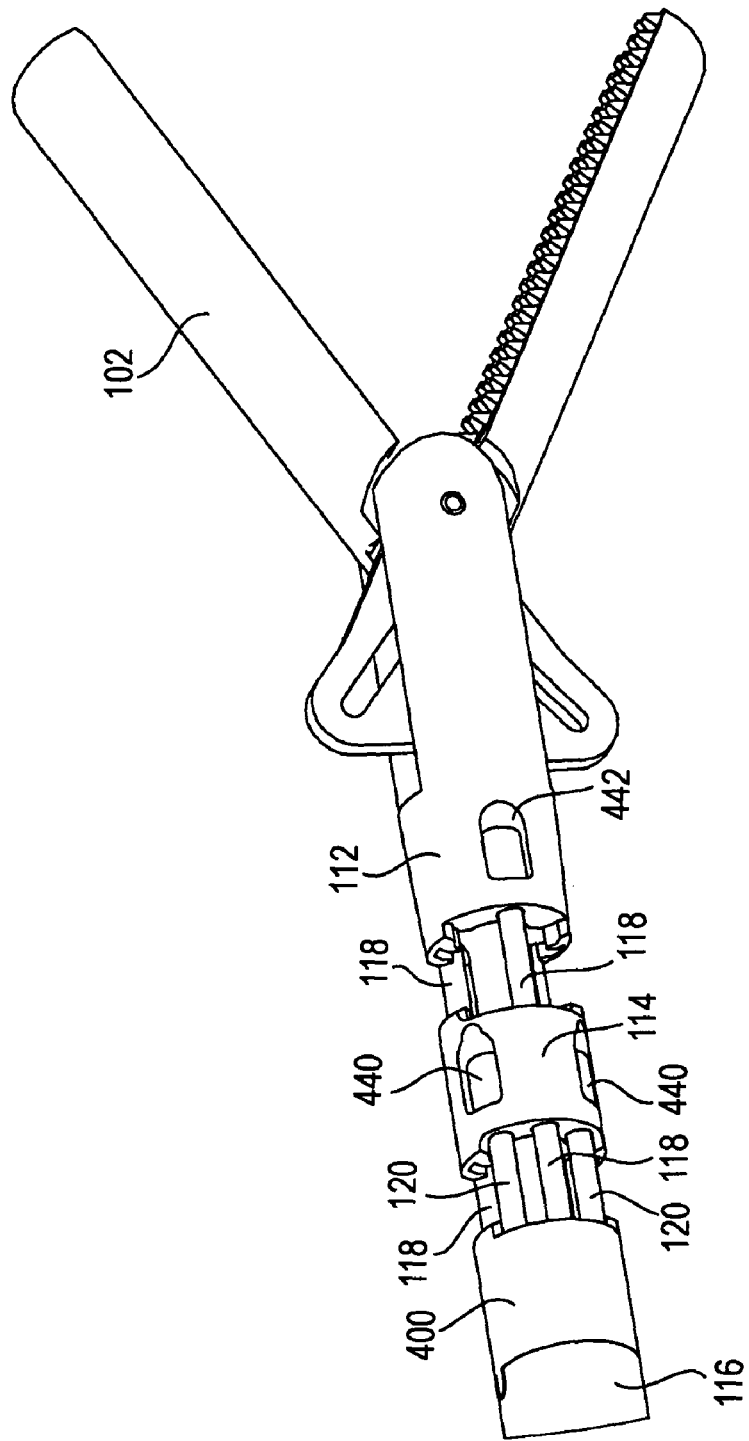
FIG. 20 is a perspective view showing a distal end of an articulating tool according to one embodiment of this invention.

As would be clear to those practiced in manufacturing arts, the threading of cables may be performed by threading either the proximal ends or the distal ends forward in their respective appropriate direction. Further, any number of cable sets may be threaded during a threading procedure, in any order. The following detailed procedure is provided merely by way of an example wherein a single cable set is threaded in a particular direction. In the embodiment shown in FIGS. 1-20, three cables 118 extend from distal link 112 to proximal link 108, and three cables 120 extend from distal link 114 to proximal link 110. Proximal ends of cables 120 may be passed through openings 440 distributed about the circumference of distal link 114 such that they emerge from the openings on the proximal face of distal link 114, as best seen in FIG. 20. Proximal ends of cables 120 may then be passed through openings 404 and channels 406 in distal end cap 400, and into channels 422 in guide 420. Channels 422 guide the proximal ends of cables 120 to channels 308 and openings 304 in proximal end cap 300, either with or without a twist, depending on the orientation of guide 420. The proximal ends of cables 120 then exit the proximal end cap 300 in the proper orientation for attachment of cables 120 and proximal link 110 to each other. Such attachment or anchoring may be accomplished by one or more of a variety of attachment methods, such as by crimping, ultrasonic welding, gluing, or by applying set screws. Some examples of these attachment methods are further described below. While FIG. 20 shows an end effector 102 with jaws, it should be understood that other kinds of end effectors or no end effector may be used with the articulating tool of this invention.

By use of an embodiment of the tension member guide 420 through any of the methods as described above, or an equivalent method, it can be understood that the threading of cables from one end (proximal or distal) of the guide to the other end (or if already assembled within a shaft, from one end of to a shaft assembly to the other end) becomes quite simple and fool proof. Inserting one of a member into an end cap opening and thence into a guide channel assures the direction of that member end to the appropriate opening on at the opposite end cap opening. Thus, a benefit of the inventive guide and associated methods relates to the creation of a significant saving of time required for assembly of the tool.

In one exemplary embodiment of cable and link attachment, the distal ends of cables 120 have enlarged portions that may be received within openings 440 as shown in FIG. 20 to prevent the distal ends from being pulled proximally through distal link 114. Likewise, the proximal ends of cables 118 are passed through openings 442 distributed about distal link 112, through distal link 114, distal end cap 400, down guide 420 through shaft 116, through proximal end cap 300 and proximal link 110, and are attached to proximal link 108. Guide 420 once again provides the proper position and orientation for cables 118.

Figure 21:
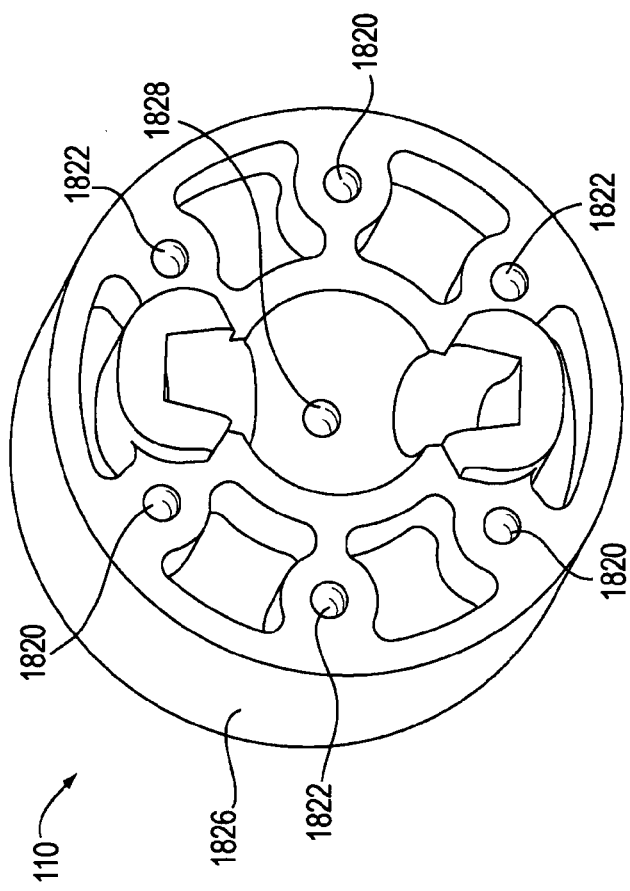
FIGS. 21 and 22 show details of a proximal link according to one embodiment of this invention.
Figure 22:
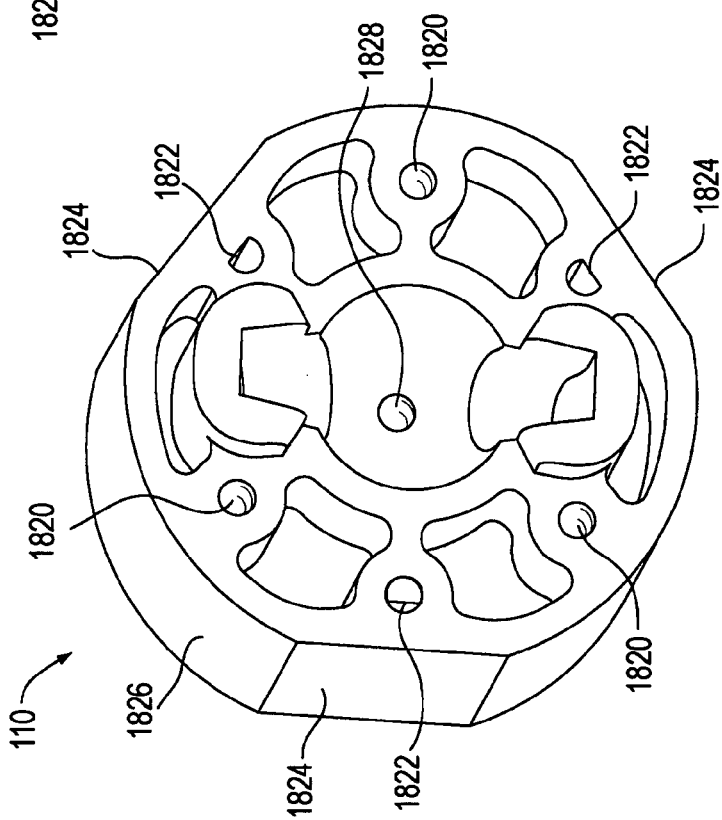

FIGS. 21 and 22 show details of one embodiment of a tension member attachment method. FIGS. 21 and 22 are distal-looking perspective views of proximal link 110 before and after, respectively, being deformed by a crimping process. Holes 1820 are provided through proximal link 110 for receiving cables 118 and holes 1822 are provided for receiving cables 120 (cables 118 and 120 can be seen in FIGS. 1, 2, 18 and 20). In the embodiment shown, cables 118 slidably pass through holes 1820 in proximal link 110 to terminate at proximal link 108 (as discussed below), and cables 120 terminate in holes 1822 of proximal link 110. To anchor cables 1822 to proximal link 110, a portion 1824 of circumferential surface 1826 may be inwardly deformed to collapse each hole 1822 (FIG. 22) onto a cable 120. Hole 1828 through the center of proximal link 110 (see FIG. 18) may be provided with an appropriately small or fitted diameter to constrain rod 125 from undesirable lateral movement, flexion, or buckling as it passes through link 110.

Figure 23:
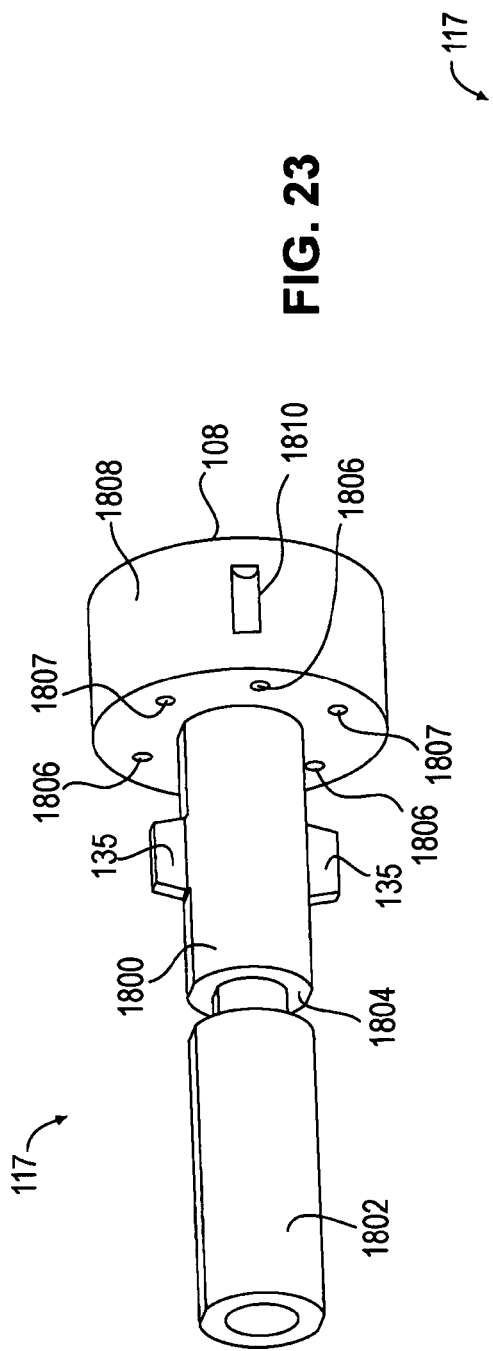
FIGS. 23 and 24 show details of another proximal link according to one embodiment of this invention.
Figure 24:
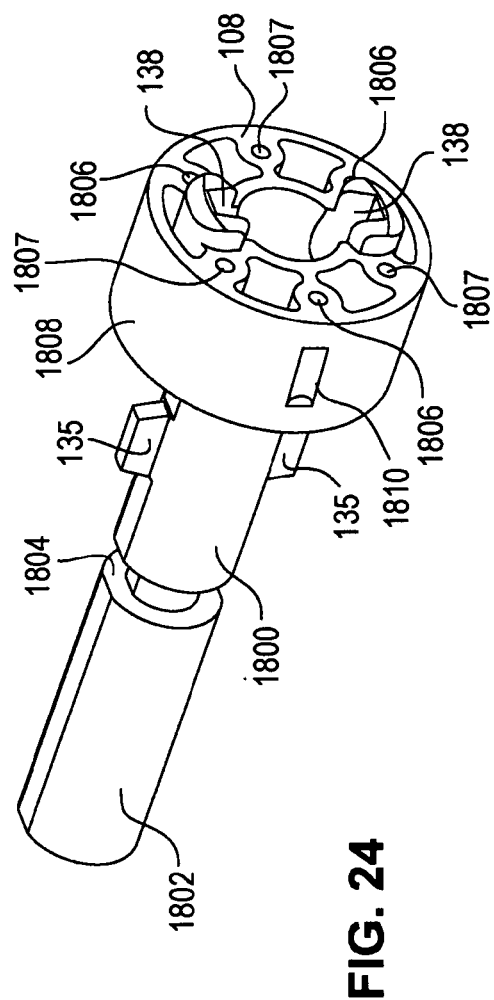

FIGS. 23 and 24 show further details a crimp as applied to proximal link 108 which is integrated with a spindle element 117. (Further details of spindle 117 may be found in co-pending US patent application titled "Articulating Tools with Rotation Lock," filed concurrently with this application.). Through holes 1806 may be provided in link 108 for receiving the proximal ends of cables 118 (shown in FIGS. 1, 2, 18 and 20) that interconnect proximal link 108 with distal link 112. In the embodiment shown in the figures, only three of the six holes of proximal link 108 are used (i.e. holes 1806 are used but holes 1807 are not). Alternatively, the proximal ends of cables 120 may pass freely through the three vacant holes 1807 of proximal link 108 after being attached to proximal link 110 as described above so that all six cables can be cut at the same location proximal to link 108. The proximal ends of cables 118 may be secured within holes 1806 of link 108 by a crimping process, such as described above in relation to FIGS. 21 and 22. Alternatively, a smaller crimping die may be pressed radially inward from the circumferential surface 1808 of link 108 to deform the material adjacent to the cable end, leaving an indentation 1810 and securing the cable end from axial movement relative to link 108.

Other means may be used to secure proximal and/or distal ends of cables 118 and 120 to links 108, 110, 112, or 114, such as soldering, ultrasonic welding, clamping, use of set screws, glue or other adhesives. Links 108, 110, 112, or 114 may be made from a variety of materials suitable for the particular attachment process used, such as metals, plastics or ceramics. Further, the side pockets for accommodating terminating cables, for example opening 440 as shown FIG. 2B in the context of distal link 114, may also be applied to cables that terminate proximal links.

While the inventive surgical instruments and devices with an improved tension member guide have been described in some detail by way of illustration, such illustration is for purposes of clarity of understanding only. It will be readily apparent to those of ordinary skill and in the art in light of the teachings herein that certain changes and modifications may be made thereto without departing from the spirit and scope of the appended claims. For example, while the tool embodiments described in here have typically been in the context of tools with an articulating mechanism comprising at least two links, the tension member guide system may be used in an instrument comprising only a single link, a multiplicity of links, and with any number of tension members such as cables, or numbers of cable sets operably connecting the links. Further, the tension member guide system may be used in tools that are absent various features that may be associated with some articulatable instruments, such as handles, rotatability features, and dedicated end effectors. Finally, while the context of the invention is considered to be surgical or medical diagnostic procedures, the tension member guide system or tool having such a system may have utility in other non-medical contexts as well.

What is claimed is:

1. An articulating tool comprising:
   a shaft having a proximal and a distal end, and an end cap located on at least one end;
   an articulation mechanism comprising a movable proximal element disposed at the proximal end of the shaft, a movable distal element disposed at the distal end of the shaft, and a plurality of tension bearing members, each member having a proximal end and a distal end, the members extending between the proximal and distal elements so that movement of the proximal element with respect to the shaft causes a corresponding movement of the distal element with respect to the shaft; and
   an elongated guide located along at least a portion of the shaft, the guide configured to guide the tension bearing members,
   the end cap disposed on an end of the shaft for guiding the plurality of tension bearing members, wherein the end cap guides each of the tension bearing members from a first radial distance to a second radial distance from a central axis, wherein the end cap comprises at least two inter-engaging parts that cooperate to form closed channels that guide each of the tension bearing members from the first radial distance to the second radial distance.

2. The tool of claim 1 wherein the guide comprises a plurality of channels extending along its length, each channel for receiving one of the plurality of tension bearing members.

3. The tool of claim 2 wherein the channels are circumferentially closed.

4. The tool of claim 2 wherein the channels comprise grooves.

5. The tool of claim 2 wherein each channel forms a generally straight path.

6. The tool of claim 2 wherein each channel forms a generally helical path.

7. The tool of claim 6 wherein each helical channel revolves about 180 degrees.

8. The tool of claim 2 wherein the guide is generally circular in cross section with the channels spaced around the circumference of the cross section.

9. The tool of claim 2 wherein the guide further comprises a central channel for receiving an additional tension bearing member.

10. The tool of claim 2 wherein the guide further comprises one or more channels for receiving one or more operable elements.

11. The tool of claim 10 wherein the one or more operable elements comprise any one or more of a compression bearing member, a tension bearing member, a wire, an optical fiber, a hydraulic tube, or a vacuum tube.

12. The tool of claim 1 wherein the guide guides at least three tension bearing members.

13. The tool of claim 1 wherein the guide guides at least six tension bearing members.

14. The tool of claim 1 wherein at least one of the tension bearing members is also a compression bearing member.

15. The tool of claim 1 wherein the shaft comprises a tube, wherein the guide has a length and a constant cross section along substantially the entire length, and wherein the guide is located within the tube.

16. The tool of claim 1 wherein the guide is made of a flexible polymer.

17. The tool of claim 1 wherein the shaft and the guide are flexible.

18. The tool of claim 1 wherein one of the movable elements, proximal or distal, is crimped so as to fixedly attach it and the corresponding end of the tension bearing member together.

19. The tool of claim 1 wherein one of the movable elements, proximal or distal, and the corresponding end of the tension bearing member are ultrasonically welded together.

20. The tool of claim 1 wherein the end cap is located adjacent to a proximal end of the shaft, and the first and second radial distances differ by a factor of about three.

21. The tool of claim 1 wherein the end cap and the guide have inter-engaging rotational alignment features.

22. A method of assembling the tool of claim 1, the method comprising:
    inserting the guide into a lumen of the shaft element;
    attaching the end cap to an end of the lumen; and
    inserting at least one of the tension bearing members through the end cap and the guide.

23. The method of claim 22 further comprising:
    rotating at least one end of the guide around a longitudinal axis relative to an opposite end of the guide; and
    fixing the relative positions of the rotated ends.

24. The method of claim 23 wherein the inserting step is performed before the rotating step.

25. The method of claim 23 wherein the rotating step is performed before the inserting step.

26. The method of claim 22 further comprising deforming the movable proximal element so as to attach the proximal element and the proximal end of the tension bearing element together.

27. The method of claim 22 further comprising deforming the movable distal element so as to attach the distal element and the distal end of the tension bearing element together.

* * * * *